(12) United States Patent
Abe

(10) Patent No.: US 10,776,416 B2
(45) Date of Patent: Sep. 15, 2020

(54) RADIATION IMAGING APPARATUS, INFORMATION PROCESSING METHOD, INFORMATION PROCESSING APPARATUS, CONTROL METHOD THEREFOR, AND COMPUTER-READABLE STORAGE MEDIUM

(71) Applicant: CANON KABUSHIKI KAISHA, Tokyo (JP)

(72) Inventor: Masahiro Abe, Yamamoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 168 days.

(21) Appl. No.: 14/983,733

(22) Filed: Dec. 30, 2015

(65) Prior Publication Data

US 2016/0196045 A1    Jul. 7, 2016

(30) Foreign Application Priority Data

Jan. 6, 2015    (JP) .................................. 2015-001077

(51) Int. Cl.
*G06F 16/583*    (2019.01)
*G06F 3/0482*    (2013.01)
(Continued)

(52) U.S. Cl.
CPC ............ *G06F 16/583* (2019.01); *A61B 6/461* (2013.01); *A61B 6/465* (2013.01); *A61B 6/467* (2013.01);
(Continued)

(58) Field of Classification Search
CPC ............ A61B 6/46; A61B 6/465; A61B 6/467; A61B 6/545; A61B 6/5294; A61B 6/461; G06F 16/583; G16H 40/63; G16H 40/67
See application file for complete search history.

(56) References Cited

U.S. PATENT DOCUMENTS 6,603,494 B1 *  8/2003  Banks .................... A61B 5/055
                                                        600/410
6,714,623 B2 *  3/2004  Sako ........................ A61B 6/00
                                                        378/115
(Continued)

FOREIGN PATENT DOCUMENTS

JP    2000-308631    11/2000
JP    2003-284709    10/2003
(Continued)

*Primary Examiner* — Ryan F Pitaro
(74) *Attorney, Agent, or Firm* — Venable LLP

(57) ABSTRACT

A radiation imaging apparatus includes one or more processors and one or more memories storing, as one or more computer programs, computer-readable instructions to be executed by the processors to be performed a process including: obtaining a first imaging protocol including one or more parameters concerning radiation imaging; searching a plurality of imaging protocols stored in a storage unit for a second imaging protocol differing in some parameters from the obtained imaging protocol; causing a display unit to display a user interface for selecting an imaging protocol as a replacement destination of the first imaging protocol from the second imaging protocol specified when the second imaging protocol is specified by the process of searching; and replacing the first imaging protocol with the selected second imaging protocol in accordance with an instruction from an operator to the user interface.

20 Claims, 5 Drawing Sheets

(51) Int. Cl.
  *A61B 6/00* (2006.01)
  *G16H 40/63* (2018.01)
  *G16H 40/67* (2018.01)

(52) U.S. Cl.
  CPC ............ *A61B 6/5294* (2013.01); *A61B 6/545* (2013.01); *G06F 3/0482* (2013.01); *G16H 40/63* (2018.01); *G16H 40/67* (2018.01)

(56) References Cited

U.S. PATENT DOCUMENTS

| | | | | |
|---|---|---|---|---|
| 6,795,572 | B1* | 9/2004 | Matsuno | G01T 1/17 382/132 |
| 7,259,729 | B2* | 8/2007 | Shastri | G06F 3/1431 345/1.2 |
| 7,684,605 | B2* | 3/2010 | Klingenbeck-Regn | A61B 6/00 378/62 |
| 7,929,740 | B2* | 4/2011 | Marshall | G06T 7/0012 382/128 |
| 2004/0240624 | A1* | 12/2004 | Shiibashi | G06Q 10/10 378/197 |
| 2005/0245804 | A1* | 11/2005 | Shinohara | A61B 6/00 600/407 |
| 2007/0162159 | A1* | 7/2007 | Ladenburger | G06F 19/325 700/17 |
| 2007/0174007 | A1* | 7/2007 | Ghosh | G06F 19/20 702/19 |
| 2007/0273697 | A1* | 11/2007 | Zaman | A61B 5/7475 345/501 |
| 2008/0049996 | A1* | 2/2008 | Marshall | G06T 7/0012 382/128 |
| 2008/0249407 | A1* | 10/2008 | Hill | A61B 8/06 600/437 |
| 2009/0225940 | A1* | 9/2009 | Aoyama | A61B 6/465 378/62 |
| 2009/0262898 | A1* | 10/2009 | Matsuno | G06F 19/327 378/116 |
| 2010/0169833 | A1* | 7/2010 | Arima | A61B 6/00 715/821 |
| 2010/0299622 | A1* | 11/2010 | Sako | G06F 19/321 715/764 |
| 2011/0052034 | A1* | 3/2011 | Watanabe | A61B 6/00 382/132 |
| 2012/0027178 | A1* | 2/2012 | Mabini | A61B 6/461 378/98 |
| 2013/0266118 | A1* | 10/2013 | Senba | A61B 6/545 378/62 |
| 2014/0013199 | A1* | 1/2014 | Buurman | G06F 19/321 715/226 |
| 2014/0098932 | A1* | 4/2014 | Profio | A61B 6/032 378/19 |
| 2014/0149910 | A1* | 5/2014 | Lee | A61B 6/465 715/771 |
| 2014/0258907 | A1* | 9/2014 | Tanaka | G06F 19/3406 715/771 |
| 2014/0304638 | A1* | 10/2014 | Yoshikawa | A61B 6/465 715/771 |
| 2015/0035723 | A1* | 2/2015 | Mori | G06F 19/1446 345/1.3 |
| 2015/0117607 | A1* | 4/2015 | Hayashi | A61B 6/463 378/62 |
| 2015/0199121 | A1* | 7/2015 | Gulaka | G06F 3/04845 715/771 |
| 2015/0272703 | A1* | 10/2015 | Arima | A61B 6/461 378/62 |
| 2015/0281564 | A1* | 10/2015 | Shin | G06F 3/04847 715/771 |
| 2015/0297157 | A1* | 10/2015 | Mukumoto | A61B 6/5205 378/15 |
| 2015/0297166 | A1* | 10/2015 | Goto | G09B 23/286 378/15 |
| 2016/0081650 | A1* | 3/2016 | Okusu | A61B 6/56 378/62 |
| 2016/0213347 | A1* | 7/2016 | Kawanishi | A61B 6/4464 |
| 2016/0361035 | A1* | 12/2016 | Lee | A61B 6/465 |

FOREIGN PATENT DOCUMENTS

| | | |
|---|---|---|
| JP | 2013-215273 | 10/2013 |
| JP | 2014-000474 | 1/2014 |

* cited by examiner

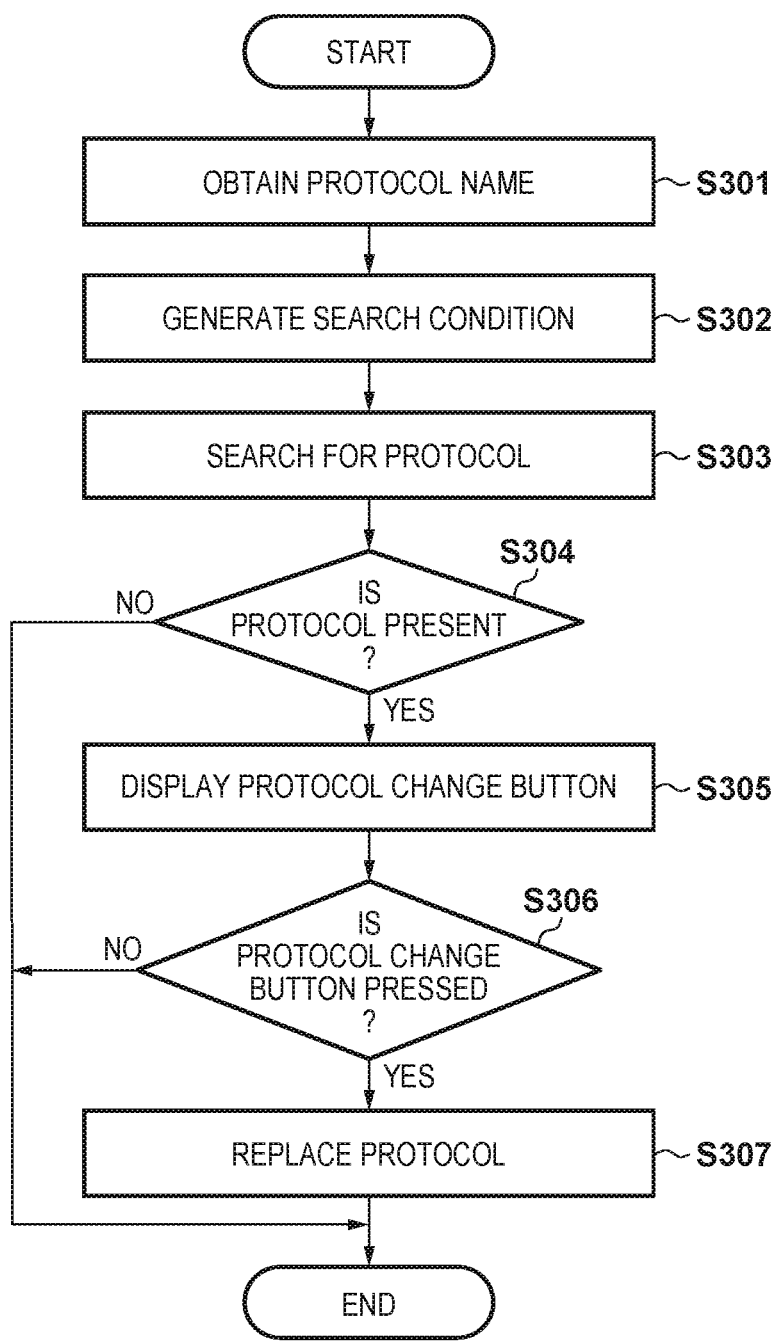

FIG. 4A

```
401  402                              403
┌─────────────────────────┬──────────────────────┐
│ PATIENT ID : 22222  TUBE VOLTAGE : V │ PATIENT ID : 22222      │
│ PATIENT NAME :      TUBE CURRENT : mA│ PATIENT NAME :          │
│ CANON JIRO                           │ CANON JIRO              │
│                                      │ BIRTH DATE 2000/02/03   │
│                                      ├─────────────────────────┤ 404
│                                      │ ACC# : 12345            │
│                                      ├─────────────────────────┤ 405
│                                      │ □ FRONT OF    ⌐L       │ 406
│                                      │   RIGHT HAND  ⌐R       │
│                                      │                         │
│                                      │                         │
│ ACC# : 12345                         │ [ END OF INSPECTION ]   │
└─────────────────────────┴──────────────────────┘
```

FIG. 4B

```
┌─────────────────────────┬──────────────────────┐
│ PATIENT ID : 22222  TUBE VOLTAGE : V │ PATIENT ID : 22222      │
│ PATIENT NAME :      TUBE CURRENT : mA│ PATIENT NAME :          │
│ CANON JIRO                           │ CANON JIRO              │
│                                      │ BIRTH DATE 2000/02/03   │
│                                      ├─────────────────────────┤
│                                      │ ACC# : 12345            │
│                                      ├─────────────────────────┤ 407
│                                      │ □ FRONT OF    ⌐L       │ 408
│                                      │   LEFT HAND   ⌐R       │
│                                      │                         │
│ ACC# : 12345                         │ [ END OF INSPECTION ]   │
└─────────────────────────┴──────────────────────┘
```

FIG. 5A

FIG. 5B

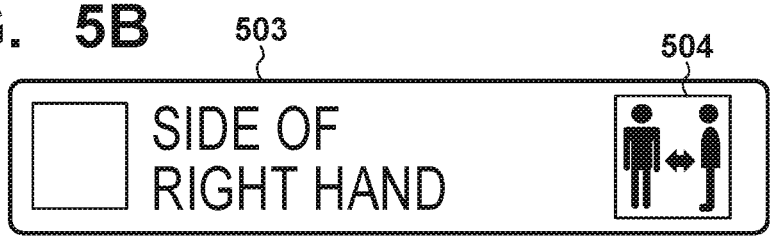

FIG. 6

| ATTRIBUTE CATEGORY | SEARCH STRING | SUBSTITUTE STRING |
|---|---|---|
| LATERALITY | LEFT | RIGHT |
| LATERALITY | RIGHT | LEFT |
| IMAGING DIRECTION | FRONT | SIDE |
| IMAGING DIRECTION | SIDE | FRONT |
| IMAGING POSTURE | STANDING POSITION | DECUBITUS POSITION |
| IMAGING POSTURE | DECUBITUS POSITION | STANDING POSITION |
| LR | Left | Right |
| LR | Right | Left |
| Orientaion | PA | LAT |
| Orientaion | LAT | PA |
| Position | Stand | Supine |
| Position | Supine | Stand |

FIG. 7

| ATTRIBUTE CATEGORY | TARGET PORTION | SEARCH CODE VALUE | CODE MEANING | SUBSTITUTE CODE VALUE | CODE MEANING |
|---|---|---|---|---|---|
| IMAGING DIRECTION | 13-14 | 02 | FRONT (A→P) | 03 | FRONT (P→A) |
| IMAGING DIRECTION | 13-14 | 03 | FRONT (P→A) | 02 | FRONT (A→P) |
| IMAGING DIRECTION | 13-14 | 05 | SIDE (R→L) | 06 | SIDE (L→R) |
| IMAGING DIRECTION | 13-14 | 06 | SIDE (L→R) | 05 | SIDE (R→L) |
| IMAGING DIRECTION | 13-14 | 67 | RIGHT SURFACE (RIGHT SIDE) | 68 | LEFT SURFACE (LEFT SIDE) |
| IMAGING DIRECTION | 13-14 | 68 | LEFT SURFACE (LEFT SIDE) | 67 | RIGHT SURFACE (RIGHT SIDE) |

FIG. 8

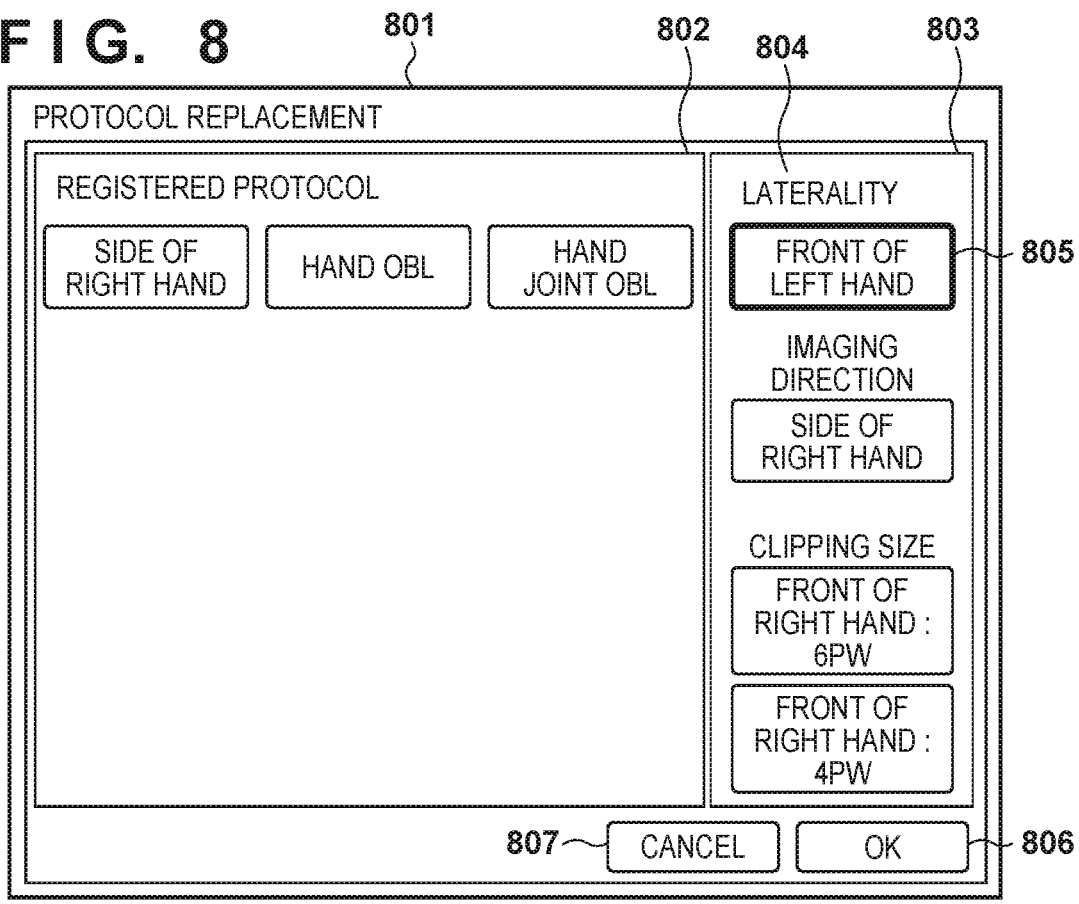

RADIATION IMAGING APPARATUS, INFORMATION PROCESSING METHOD, INFORMATION PROCESSING APPARATUS, CONTROL METHOD THEREFOR, AND COMPUTER-READABLE STORAGE MEDIUM

BACKGROUND OF THE INVENTION

Field of the Invention

The present invention relates to a radiation imaging apparatus, an information processing method, an information processing apparatus, a control method therefor, and a computer-readable storage medium and, more particularly, to a radiation imaging apparatus for obtaining a medical radiation image.

Description of the Related Art

Recently, there has been a proliferation of an X-ray imaging system using an X-ray sensor such as a flat panel detector which converts an X-ray signal into a digital image and outputs it. Before imaging, a general X-ray imaging system registers an imaging protocol for an inspection based on a manual operation or deploys an imaging protocol based on an imaging order notified from an RIS (Radiology Information System) and registers it for the inspection. When an inspection starts, the technician performs X-ray imaging upon checking the positioning of a patient, X-ray generation conditions, and the like based on the registered imaging protocol (see Japanese Patent Laid-Open No. 2000-308631). Note that the imaging protocol is information which defines radiation imaging, including parameters indicating imaging conditions and the contents and the like of image processing to be performed for an obtained image.

An imaging protocol deployed by an imaging order is sometimes replaced with another imaging protocol in accordance with the determination made by the technician when actually performing imaging. For example, since a patient on a wheelchair cannot be imaged in a standing position, the imaging protocol is replaced with an imaging protocol for a sitting position. Imaging protocol replacement may be performed when, for example, the technician wants to intentionally change a body part, an imaging order itself is wrong, or an imaging protocol added on site is wrong. Such imaging protocols are replaced according to several replacement patterns such as a pattern of interchanging "left" and "right" within the same body part and a pattern of interchanging irradiation directions.

Conventionally, in order to simplify replacement of imaging protocols, a list of imaging protocols as substitute candidates registered in advance with respect to a given imaging protocol is displayed, and the operator (user) selects a displayed substitute candidate protocol. If, however, all substitute candidates are registered assuming all kinds of errors in imaging protocols, the number of substitute candidates becomes enormous, and it takes much time and effort to register them. Besides, the number of choices excessively increases, and it takes much time and effort to search for and select a desired imaging protocol from the substitute candidates. Assume that protocol substitute candidates are limited to representatives, and an imaging protocol is replaced to correct a mistake concerning "left" and "right". Even in this case, it is necessary to perform an operation of searching all registered protocols, resulting in poor operability.

SUMMARY OF THE INVENTION

The present invention has been made in consideration of the above problem and provides a technique of allowing a radiation imaging system to easily change imaging protocols.

According to one aspect of the present invention, a radiation imaging apparatus includes: one or more processors; one or more memories storing, as one or more computer programs, computer-readable instructions to be executed by the one or more processors to be performed a process including: obtaining a first imaging protocol including one or more parameters concerning radiation imaging; searching a plurality of imaging protocols stored in a storage unit for a second imaging protocol differing in some parameters from the obtained imaging protocol; causing a display unit to display a user interface for selecting an imaging protocol as a replacement destination of the first imaging protocol from the second imaging protocol specified when the second imaging protocol is specified by the process of searching; and replacing the first imaging protocol with the selected second imaging protocol in accordance with an instruction from an operator to the user interface.

According to another aspect of the present invention, an information processing apparatus which controls an operation of a radiation generator adapted to irradiate an object with radiation and an operation of a sensor adapted to form an image upon detecting the radiation, the apparatus includes: an obtaining unit adapted to obtain a first imaging protocol including one or more parameters concerning radiation imaging; a search unit adapted to search a plurality of imaging protocols stored in a storage unit for a second imaging protocol differing in some parameters from the obtained imaging protocol; a control unit adapted to cause a display unit to display a user interface for selecting an imaging protocol as a replacement destination of the first imaging protocol from the second imaging protocol specified when the second imaging protocol is specified by the search unit; and a replacement unit adapted to replace the first imaging protocol with the selected second imaging protocol in accordance with an instruction from an operator to the user interface.

According to still another aspect of the present invention, an information processing method for performing a radiation imaging exposing an object to radiation to obtain a radiation image, the method includes: causing an obtaining unit to obtain a first imaging protocol including one or more parameters concerning radiation imaging; causing a search unit to search a plurality of imaging protocols stored in a storage unit for a second imaging protocol differing in some parameters from the obtained imaging protocol; causing a control unit to cause a display unit to display a user interface for selecting an imaging protocol as a replacement destination of the first imaging protocol from the second imaging protocol specified when the second imaging protocol is specified in the searching; and causing a replacement unit to replace the first imaging protocol with the selected second imaging protocol in accordance with an instruction from an operator to the user interface.

According to yet another aspect of the present invention, a control method for an information processing apparatus which controls an operation of a radiation generator adapted to irradiate an object with radiation and an operation of a sensor adapted to form an image upon detecting the radiation, the method includes: causing an obtaining unit to obtain a first imaging protocol including one or more parameters concerning radiation imaging; causing a search unit to search a plurality of imaging protocols stored in a storage unit for a second imaging protocol differing in some parameters from the obtained imaging protocol; causing a control unit to cause a display unit to display a user interface for selecting an imaging protocol as a replacement destination of the first imaging protocol from the second imaging protocol specified when the second imaging protocol is specified in the searching; and causing a replacement unit to replace the first imaging protocol with the selected second imaging protocol in accordance with an instruction from an operator to the user interface.

According to still yet another aspect of the present invention, a non-transitory computer-readable storage medium storing a computer program for causing a computer to function as each unit of a radiation imaging apparatus includes: an obtaining unit adapted to obtain a first imaging protocol including one or more parameters concerning radiation imaging; a search unit adapted to search a plurality of imaging protocols stored in a storage unit for a second imaging protocol differing in some parameters from the obtained imaging protocol; a control unit adapted to cause a display unit to display a user interface for selecting an imaging protocol as a replacement destination of the first imaging protocol from the second imaging protocol specified when the second imaging protocol is specified by the search unit; and a replacement unit adapted to replace the first imaging protocol with the selected second imaging protocol in accordance with an instruction from an operator to the user interface.

Further features of the present invention will become apparent from the following description of exemplary embodiments (with reference to the attached drawings).

BRIEF DESCRIPTION OF THE DRAWINGS

FIG. 3 is a flowchart showing a procedure for processing executed by the radiation imaging system;

FIGS. 4A and 4B are views each showing an example of a GUI in the radiation imaging system;

FIGS. 5A and 5B are views each showing an example of a GUI for switching parameters of imaging protocols;

FIG. 6 is a view showing an example of setting information;

FIG. 7 is a view showing an example of setting information; and

FIG. 8 is a view showing an example of a GUI in the radiation imaging system.

DESCRIPTION OF THE EMBODIMENTS

The embodiments of the present invention will be described below with reference to the accompanying drawings. The following embodiments do not limit the present invention according to the appended claims, and not all combinations of characteristic features described in the embodiments are essential to the present invention.

(Radiation Imaging System)

Figure 1:
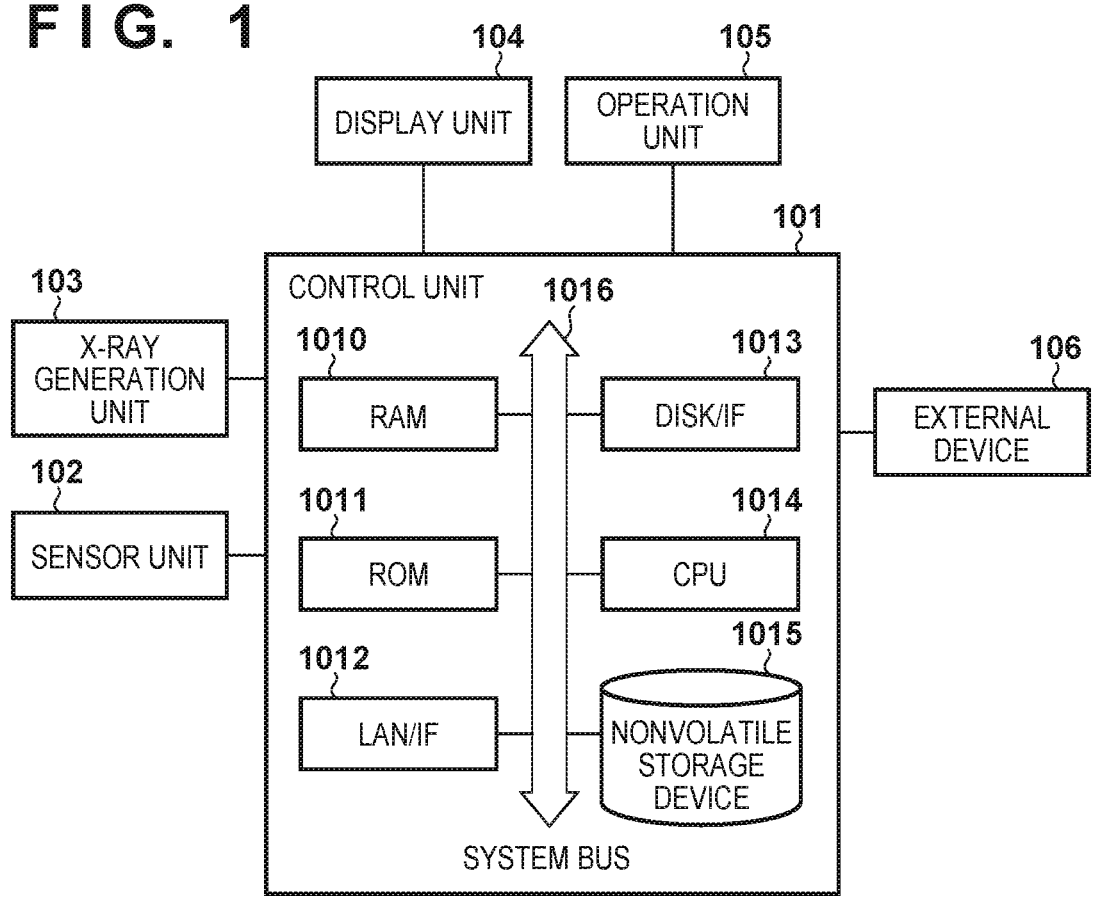
FIG. 1 is a block diagram showing the hardware arrangement of a radiation imaging system.

FIG. 1 is a block diagram showing an example of the hardware arrangement of a radiation imaging system according to an embodiment of the present invention. Referring to FIG. 1, a control unit 101 includes a RAM 1010, a ROM 1011, a LAN/IF 1012, a DISK/IF 1013, a CPU 1014, and a nonvolatile storage device 1015. These components are connected to each other via a system bus 1016.

The RAM 1010 is a writable memory, which is used as a work area for arithmetic processing. The ROM 1011 is a read-only memory, which stores basic programs, basic data, and the like. The LAN/IF 1012 is a communication interface via which the control unit 101 communicates with an external device. This embodiment will exemplify a case in which communication is performed via a LAN (Local Area Network). However, it is possible to perform communication via other communication schemes such as wireless LAN and Bluetooth®. The DISK/IF 1013 is an interface for accessing a recording medium for recording data, computer programs, and the like. Although the embodiment will exemplify a case in which an FD (Flexible Disk) is used as a recording medium, other recording media such as a CD, a DVD, a BD, a USB memory, and a flash memory may be used. The CPU 1014 is a central processing unit, which controls the operation of each constituent element connected to the system bus 1016 based on computer programs such as an OS (Operating System). The nonvolatile storage device 1015 is a large-capacity storage device, which stores the OS, application programs, various types of data concerning imaging, and the like. In this embodiment, the nonvolatile storage device 1015 is implemented by a hard disk. However, it is possible to use, as this device, an SSD (Solid State Drive) or an arbitrary storage device capable of storing data, such as a magnetic tape. As described above, the control unit 101 has a general computer arrangement.

The control unit 101 drives a sensor unit 102 and controls an X-ray generation unit 103 based on an input operation by the operator via an operation unit 105. The control unit 101 also manages various type of data such as imaging protocol data and image data. The control unit 101 can be implemented by an information processing apparatus such as a PC (Personal Computer) or a tablet terminal.

The operation unit 105 is constituted by input devices such as a pointing device, a keyboard, and an irradiation switch, and is used by the operator to input various types of commands and data to the control unit 101. A display unit 104 is formed from a general monitor such as a CRT or liquid crystal display, which displays image data, a GUI (Graphical User Interface), and the like on the screen. In addition, the display unit can also be formed from a monitor also having the input function of the operation unit 105, such as a touch panel.

The X-ray generation unit 103 is an X-ray generator (radiation generator). The X-ray generation nit 103 causes an X-ray tube (not shown) to apply X-rays toward the sensor unit 102 via an object in accordance with an operation such as pressing an exposure button (not shown) of the X-ray generator. Although this embodiment will exemplify a case in which X-rays are used as typical radiation used for imaging, radiation having other wavelengths may be used.

The sensor unit 102 is a sensor unit which detects an X-ray signal transmitted through an object and forms/obtains a radiation image, and transfers the obtained image to the control unit 101. An external device 106 is a system which acquires/manages obtained images, and includes general external systems capable of DICOM communication. The external device 106 is typified by, for example, an RIS as a source of imaging orders or a PACS (Picture Archiving and Communication System) for archiving and displaying obtained images.

Figure 2:
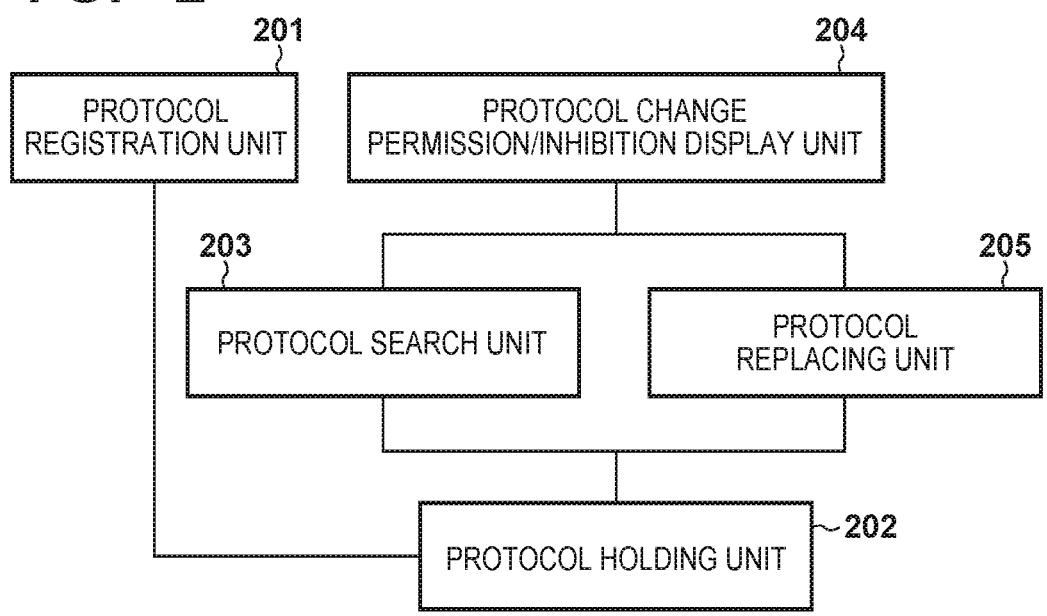
FIG. 2 is a block diagram showing the functional arrangement of the radiation imaging system.

The function arrangement of the radiation imaging system according to this embodiment will be described next with reference to FIG. 2. FIG. 2 is a block diagram showing the functional arrangement of the radiation imaging system according to the embodiment. Although the respective functional elements shown in FIG. 2 are implemented by making the control unit 101 perform arithmetic processing based on computer programs, some or all of the functional elements may be implemented by dedicated hardware.

A protocol registration unit 201 is a functional block for inputting and registering a parameter associated with an imaging protocol together with a protocol name. The protocol registration unit 201 registers and obtains an imaging protocol including one or more parameters concerning radiation imaging via input devices such as the mouse and keyboard of the operation unit 105. The attribute of a parameter concerning an imaging protocol can include at least any of, for example, an imaging direction, a body part of an object, laterality, an object size, the posture of the object, a clipping size, an irradiation condition for radiation (X-rays or the like), and an image processing condition. However, this is not exhaustive. Although this embodiment will exemplify a case in which an imaging protocol is registered and obtained by an input operation by the operator, an imaging protocol may be obtained by reading it out from a storage device such as a recording medium or by communication from an external apparatus via the LAN/IF 1012.

A protocol holding unit 202 has a function of permanently holding/storing protocol information input by the protocol registration unit 201 in a database constructed in the nonvolatile storage device 1015. A protocol search unit 203 is a functional block for searching for an imaging protocol stored in the protocol holding unit 202 based on a predetermined condition. More specifically, the protocol search unit 203 searches a plurality of imaging protocols held in the protocol holding unit 202 for an imaging protocol obtained by replacing some parameters of an imaging protocol registered/obtained by the protocol registration unit 201 with different parameters. The protocol search unit 203 is implemented by a computer program loaded into a memory (RAM 1010 or the like) in the control unit 101.

A protocol change permission/inhibition display unit 204 is a functional block for displaying a GUI on the display unit 104 based on a search result obtained by the protocol search unit 203. That is, when an imaging protocol with some parameters being replaced is searched out, a control is performed to display, on the display device, a GUI for replacing some parameters of the imaging protocol obtained by the protocol registration unit 201 with different parameters for each attribute.

A protocol replacing unit 205 is a unit having a role of performing imaging protocol replacement processing based on an instruction input by the user. That is, the protocol replacing unit 205 replaces the imaging protocol obtained by the protocol registration unit 201 with the imaging protocol with some parameters being replaced with different parameters in accordance with an instruction issued by the operator with respect to the GUI.

In this embodiment, when an imaging protocol is specified, a search is made for an imaging protocol obtained by replacing some parameters of the specified imaging protocol with different parameters, and a GUI for replacing some parameters is generated and displayed in a selectable state in accordance with a search result. This allows the operator to easily replace the imaging protocol with a desired imaging protocol without selecting it from a list of all replaceable imaging protocols or registering substitute candidates in advance.

(Processing Procedure)

A procedure for processing according to this embodiment will be described next with reference to FIG. 3. FIG. 3 is a flowchart showing a procedure for processing executed by the radiation imaging system according to the embodiment. This procedure indicates a typical processing procedure between when a protocol change button is displayed with respect to a given imaging protocol and when the imaging protocol is replaced by pressing the button. Note that the procedure is based on the assumption that imaging protocols are registered in the protocol holding unit in advance. Each of the following steps is executed under the control of the CPU 1014.

In step S301, an imaging protocol name is obtained as a target for which it is decided whether to display a change permission/inhibition button. In general, all the imaging protocols registered for inspections can be targets. Alternatively, a target may be an imaging protocol selected for imaging to be performed. As described above, it is possible to specify an imaging protocol by using any method. In this step, after an imaging protocol as a target is specified, the protocol name of the imaging protocol is obtained.

In step S302, a search condition is generated to search for an imaging protocol with some parameters as attributes being different from the imaging protocol name obtained in step S301. If, for example, the imaging protocol "front of right hand" is specified in step S301, the string "front of left hand" is generated by replacing the parameter "right" with "left" to search for an imaging protocol having a different left/right attribute. In step S303, a search is executed in the protocol holding unit 202 based on the search string generated in step S302.

In step S304, control is performed to branch between processing contents based on the result obtained in protocol search step S303. If there is an imaging protocol matching the search condition generated in step S302 (YES in step S304), the process advances to step S305. If there is no such protocol (NO in step S304), the processing is terminated.

In step S305, the protocol change button is displayed as a GUI. In step S306, control is performed to branch between processing contents by determining whether the button displayed in step S305 is pressed. If the button is pressed (YES in step S304), the process shifts to step S307. If the button is not pressed (NO in step S304), the processing is terminated without performing any processing.

In step S307, the current imaging protocol is replaced with the imaging protocol found in step S303. In the above case, the imaging protocol "front of right hand" is changed to the imaging protocol "front of left hand". The processing is then terminated.

(GUI Example)

A GUI example of the radiation imaging system according to this embodiment will be described next with reference to FIGS. 4A and 4B. FIGS. 4A and 4B each show an example of a GUI immediately after the start of an inspection by the radiation imaging system. FIG. 4A shows a GUI example before the pressing of the protocol change button. FIG. 4B shows a GUI example after the pressing of the protocol change button.

Each GUI example includes an operation screen 401 and an image display area 402. FIGS. 4A and 4B each show a state in which no image displayed in the image display area 402 because imaging has not yet be done. Each GUI example includes an area 403 which displays information of a patient who is an object to be examined in this case. Each of the examples shown in FIGS. 4A and 4B shows a case in which the patient ID is "22222", the patient name is "Canon Jiro", and the birth date of the patient is Feb. 3, 2000.

This example includes an inspection information display portion 404, which is an area for displaying an accession number ("ACC #" in FIGS. 4A and 4B) which identifies an inspection. In each of the examples shown in FIGS. 4A and 4B, the accession number is "12345". The example includes a protocol display portion 405. The example shown in FIG. 4A indicates that the current imaging operation is for an inspection in which imaging of "front of right hand" is planned.

This example includes a protocol change button 406. In this example, this button is an example of a button displayed in step S305 if the imaging protocol "front of left hand" is found in step S304. The example includes a protocol display portion 407 after pressing of the protocol change button 406, which indicates how the imaging protocol "front of right hand" is switched to the imaging protocol "front of left hand", and a protocol change button 408 corresponding to the protocol "front of left hand". Pressing this button can switch from "front of left hand" to "front of right hand", thus returning to the state in FIG. 4A again.

As described above, the radiation imaging system according to this embodiment obtains an imaging protocol (the first imaging protocol) including one or more parameters concerning radiation imaging. This system searches a plurality of imaging protocols stored in the storage device for an imaging protocol (the second imaging protocol) differing in some parameters from the obtained imaging protocol. When the second imaging protocol is specified by the search, the system displays, on the display unit, a user interface for selecting an imaging protocol as a replacement destination of the first imaging protocol from the specified second imaging protocol. The system replaces the first imaging protocol with the selected second imaging protocol in accordance with an instruction from the operator to the user interface. This allows the operator to easily replace the first imaging protocol with a desired imaging protocol.

In addition, upon obtaining the protocol name of an imaging protocol, the radiation imaging system according to this embodiment generates a search condition based on the protocol name, and searches for an imaging protocol obtained by replacing some parameters of the above imaging protocol with different parameters. The system generates a protocol change button for replacing some parameters in accordance with a search result, and displays the button so as to allow the operator to select it. This allows the operator to easily switch from a given imaging protocol to another imaging protocol differing in parameters concerning some attributes from the given imaging protocol without performing any cumbersome operation such as searching a list of all replaceable imaging protocols for a desired imaging protocol. It is therefore expected to improve the operability for imaging protocol replacement processing and to shorten the time required for system installation because of no necessity to register substitute candidates in advance.

In addition, this embodiment is configured to automatically generate a search condition based on a protocol name and search for an imaging protocol with some parameters being replaced with different parameters based on the search condition. This makes it possible to present an imaging protocol as a substitute candidate without requiring any operation by the operator. It is therefore possible to improve the operability without requiring any cumbersome operation by the operator or system administrator.

Furthermore, this embodiment is configured to cause the display unit 104 to display, for each attribute, an icon (protocol change button) for replacing parameters of the first imaging protocol with other parameters on the protocol display portion 405 in a selectable state. In accordance with the selection of the icon by the operator, the first imaging protocol is replaced with the second imaging protocol with a parameter concerning the attribute of the icon being replaced with another parameter. Therefore, according to this embodiment, the operator can easily replace parameters included in an imaging protocol.

Assume that as a result of a search for an imaging protocol differing in some parameters from the first imaging protocol, no imaging protocol differing in some parameters from the first imaging protocol is specified. In this case, a user interface may be configured to inhibit imaging protocol replacement. For example, the protocol change button may not be displayed in the protocol display portion 405 or replacement by a manual input operation may be inhibited even if the protocol change button is displayed. This can reduce the possibility of operation errors.

The above embodiment has exemplified the case in which a search is made for an imaging protocol differing from a given imaging protocol in the parameter "laterality" indicating left/right of attributes associated with the given imaging protocol. However, an attribute as a replacement target is not limited to "laterality". Similar processing can be performed with respect to an arbitrary attribute such as an X-ray imaging condition, an image processing condition, a body part, or an imaging direction. The following will describe an example of performing parameter replacement with respect to an imaging direction, such as changing "front of left hand" to "side of left hand".

FIGS. 5A and 5B each show a display example of a button used to switch to an imaging protocol with a different imaging direction. FIGS. 5A and 5B respectively show the states of the imaging protocol display area before and after switching. A protocol display area 501 indicates an imaging protocol for imaging of "front of right hand". A protocol change button 502 indicates that it is possible to switch to an imaging protocol with a different imaging direction. An imaging protocol state indicated by reference numeral 503 is a state after pressing of the protocol change button 502, showing a state in which the imaging protocol "front of right hand" is switched to the imaging protocol "side of right hand". A button 504 is used to switch from the protocol "side of right hand" to an imaging protocol with a different imaging direction. When this button is pressed, the current state returns to the state shown in FIG. 5A.

In this manner, a GUI for parameter replacement is generated and displayed with respect to a parameter for an attribute other than "laterality" by automatically searching for a parameter as a substitute candidate as in the above embodiment. This makes it possible to improve the operability by facilitating the selection of an imaging protocol as a replacement destination without requiring any preparations such as registering substitute candidates in advance.

Setting a search string generation rule in advance can implement a more flexible operation when implementing the processing of interchanging strings indicating "left" and "right" or interchanging strings indicating imaging directions to generate a search condition string. For example, a string indicating "left/right" in English is "hidari/migi" in Japanese, and hence fixed string replacement processing is difficult to cope with various applications. For this reason, setting a rule for generating search strings in advance can generate search strings more flexibly.

FIG. 6 shows an example of set values to be used when generating a search string. "Attribute Category", "Search String", and "Substitute String" are defined as settings. "Attribute Category" indicates the categories of attributes as replacement targets of parameters associated with imaging protocols. "Search String" as setting information indicates a string for specifying a search target having the imaging protocol name of a replacement source instead of a search string with respect to the protocol holding unit 202. In the case shown in FIG. 6, laterality, an imaging direction, and an imaging posture are defined as categories. Assume that "front" and "side" are defined as imaging directions shown in FIG. 6. In this case, when "front of chest" is obtained as a protocol name, a protocol name to be generated as a search condition for substitute candidates is "side of chest". In contrast, with respect to "side of chest", "front of chest" is a search string target. An attribute category is defined to prevent the generation of search strings over a plurality of attributes. For example, if search strings are generated based on the set values in FIG. 6 with respect to the imaging protocol "front of left hand", there are three variations including "side of left hand", "front of right hand", and "side of right hand". For this reason, generating a search string individually for each attribute category makes it possible to uniquely decide "front of right hand" as laterality and "side of left hand" as an imaging direction. Note that, referring to FIG. 6, PA is an abbreviation of "Posterior-Anterior view", and LAT is an abbreviation of "Lateral".

As described above, in this embodiment, information representing the relationship between a parameter as a replacement target and a parameter after replacement is held as search condition generation rule information for each attribute of a parameter. Based on this generation rule information, a search is made for an imaging protocol as a search target obtained by replacing some parameters of an imaging protocol obtained in the protocol registration unit 201 with different parameters. This makes it possible to exhaustively and properly search for imaging protocols as substitute candidates.

In addition, if a plurality of candidates are conceivable, a protocol change button is displayed for each attribute to allow the operator to replace a given imaging protocol with a desired imaging protocol by pressing a corresponding attribute button. That is, an imaging protocol obtained by replacing a plurality of parameters of the parameters constituting an imaging protocol registered in the protocol registration unit 201 may be set as a search target. In this case, the protocol change permission/inhibition display unit 204 displays protocol change buttons equal in number to replaceable parameters as a GUI to allow the operator to change a parameter for each attribute.

In addition, a specific parameter combination may not be adopted depending on the arrangement of the radiation imaging system. For this reason, the protocol change permission/inhibition display unit 204 may inhibit the operator from selecting a parameter combination which cannot be adopted from the system viewpoint by performing control to inhibit the selection of a protocol change button, as needed, based on a search result obtained by the protocol search unit 203. Assume that the protocol registration unit 201 has registered an imaging protocol including parameters a1 and b1 with respect to two attributes A (adoptable parameters a1 and a2) and B (adoptable parameters b1 and b2). Assume also that, with regard to this imaging protocol, the protocol search unit 203 has searched out an imaging protocol including the parameters a1 and b2 and an imaging protocol including the parameters a2 and b1 (that is, an imaging protocol including the parameters a2 and b2 cannot be adopted from the system viewpoint). In this case, the protocol change permission/inhibition display unit 204 displays two protocol change buttons for replacing the parameters of attributes A and B in accordance with a search result on the imaging protocol including the parameters a1 and b1. In this case, when an instruction is issued to replace the parameters of attribute A, an imaging protocol as a replacement destination includes the parameters a2 and b1. In addition, since the combination of the parameters a2 and b2 cannot be adopted, the parameters of attribute B cannot be further replaced. For this reason, when an instruction is issued to replace the parameters of attribute A, the protocol change button for attribute B may be hidden or information indicating that no selection can be performed with respect to attribute B. Controlling the display of protocol change buttons in accordance with a search result in this manner allows the operator to easily select an imaging protocol as a replacement destination within the range of imaging protocols as substitute candidates searched out by the protocol search unit 203.

It is also possible to set a rule, by using a regular expression or the like, which searches for the addition of a specific string as well as replacing part of the string of a protocol name when generating a search string. Any setting method can be used as long as a rule for generating a search string can be defined based on an imaging protocol name.

Some facility performs a code operation of assigning the meaning of imaging information to each digit of a code value (CodeValue) for specifying an imaging protocol. For example, a code known as JJ1017 is assigned with a meaning by using a numerical value designating a procedure, body part, posture, imaging direction, or the like at each digit of a code value. In such an operation, it is possible to execute a precise and accurate search by generating a code value as a search condition instead of generating a search condition based on a protocol name. For example, the 13th and 14th bits of the code value of JJ1017 indicate an imaging direction; the code "02" of the portion is defined as "front (A→P)", and the code "03" is defined as "front (P→A)". Using these definitions makes it possible to search for an imaging protocol by generating a search code value for a code value.

FIG. 7 shows a setting table for generating search strings in this embodiment. The setting table is provided with search code values for interchanging code values with each other and substitute code values as well as settings indicating target portions of code values. In addition, since it is difficult to understand the meanings of the respective numerical values, code meanings are written in correspondence with the respective code values. The following is an operation example when using this setting table. Assume that the code value "1111111111110211" is assigned to the imaging protocol "front of chest: AP". In this case, the 13th and 14th bits "02" are a search target string, and the code "1111111111110311" obtained by replacing the string with "03" becomes a code value indicating "front of chest: PA". A search is then made in the database based on the code value.

A processing procedure in this embodiment is the same as that shown in FIG. 3; this processing can be performed following the same procedure except that "obtain protocol name" in step S301 is replaced with "obtain code value".

As described above, in this embodiment, an imaging protocol is obtained as an identification code, and a search is made for an identification code obtained by replacing a partial code value of the identification code with another code value as an imaging protocol with some parameters being replaced with different parameters. This makes it possible to properly search for an imaging protocol as a substitute candidate by using an existing identification code value.

The above embodiment is configured to superimpose a protocol change button on the imaging protocol display area to enable switching to an arbitrary imaging protocol. On the other hand, facilitating switching in this manner increases the risk of erroneously switching a protocol. For this reason, a screen for displaying protocol substitute candidates may be additionally provided to make it possible to simultaneously present protocol substitute candidates registered in advance and an imaging protocol dynamically searched out for each attribute category.

FIG. 8 shows an example of a screen which displays such protocol substitute candidates. FIG. 8 shows an example of displaying substitute candidates for the imaging protocol "front of right hand" as search targets.

This example includes a protocol substitute candidate display window 801, an area 802 for displaying substitute candidates set in advance with respect to a target imaging protocol, and an area 803 for displaying an imaging protocol searched out with respect to the target imaging protocol by the procedure in FIG. 3. That is, the area 803 is a dynamically searched-out protocol display area, which displays nothing when no imaging protocol is found as a result of a search.

An area 804 for displaying an attribute category is displayed together with a searched-out imaging protocol 805. FIG. 8 shows that "front of left hand" is presented as an imaging protocol with different laterality and set in a selected state. In addition, "side of right hand" is displayed as an imaging protocol candidate with a different imaging direction. Furthermore, "clipping size" is displayed as an attribute category, and imaging protocol buttons with different clipping sizes are displayed as candidates.

Using such a display form can indicate imaging protocol candidates in an easily understood manner even when a plurality of candidates are found by a search. A button 806 is used to confirm settings. A button 807 is used to cancel settings and close the screen.

As described above, this embodiment is configured to register imaging protocols as substitute candidates in advance for each imaging protocol and further search for an imaging protocol as a substitute candidate registered with respect to an imaging protocol obtained by the protocol registration unit 201. The embodiment is also configured to cause the display unit 104 to display an imaging protocol as a searched-out substitute candidate in a selectable state. When the operator selects the imaging protocol as the substitute candidate, the obtained imaging protocol is replaced with the selected imaging protocol. This allows the operator to also select an imaging protocol from substitute candidates registered in advance. The operator can therefore easily select an imaging protocol as a substitute candidate from more choices.

Note that each embodiment described above has exemplified the arrangement configured to search for a substitute candidate in accordance with a specified imaging protocol and display a protocol change button (icon) for replacing parameters so as to easily select a desired imaging protocol. In addition, it is possible to allow the operator to select between the operation mode of easily selecting an imaging protocol in this manner and the operation mode of displaying a list of imaging protocols held in the protocol holding unit 202 on the display unit 104 in a selectable state and replacing the target protocol with a selected imaging protocol. That is, when the second imaging protocols are specified by a search, the display unit displays the first user interface for selecting an imaging protocol as a replacement destination of the first imaging protocol from the specified second imaging protocols (simple selection mode). In addition, in accordance with an instruction from the operator, the display unit displays the second user interface for selecting an imaging protocol as a replacement destination from a list of a plurality of imaging protocols stored in the storage device (list-based selection mode). The first imaging protocol may be replaced with an imaging protocol selected based on at least either of the first and second user interfaces. This allows the operator to switch between simple selection of a substitute protocol and exhaustive selection from a displayed list in accordance with the application/purpose. This can further improve the operability. Note that it is possible to switch between the operation modes in accordance with an instruction from the operator who has selected a switching button displayed on the display unit 104 in a selectable state. In addition, imaging protocols to be displayed in the form of a list may be imaging protocols searched out by the protocol search unit 203 instead of all the imaging protocols held in the protocol holding unit 202. This will narrow down the number of selectable imaging protocol candidates and hence allows the operator to easily select an imaging protocol. In addition, the first user interface via which it is possible to easily select an imaging protocol with an icon is displayed on the protocol display portion 405, and the second user interface via which it is possible to select an imaging protocol from a list of imaging protocols may be displayed in the image display area 402. This allows the operator to selectively use these two user interfaces as needed.

Note that in the list-based selection mode, when an imaging protocol is replaced, image processing is generally redone in accordance with image processing parameters associated with the imaging protocol as the replacement destination. For this reason, in the list-based selection mode, it often takes several sec to display a new radiation image corresponding to an imaging protocol after replacement after an imaging protocol as a replacement destination is selected. In contrast to this, in the simple selection mode, when a body part remains the same after the replacement of an imaging protocol, since it is not necessary to perform correction by image processing, an image can be quickly displayed after the replacement. In the simple selection mode, however, when a body part or direction changes upon replacement and image processing parameters change, since it is necessary to redo image processing, it takes several sec to display a properly processed image.

In addition, a user interface via which it is possible to easily select an imaging protocol as a replacement destination by using a protocol change button may be turned on/off by a setting. That is, when the operator makes an ON setting, an imaging protocol is searched out, and a user interface is displayed in accordance with the flowchart of FIG. 3. When an OFF setting is made, it is possible to inhibit the execution of a search or the display of a user interface. This makes it possible to select various types of imaging protocols in accordance with applications or purposes.

Furthermore, according to the flowchart of FIG. 3, if an imaging protocol as a replacement destination is found by a protocol search in step S303, a protocol change button is displayed (in step S304 (YES) and step S305). However, a protocol change button may be displayed regardless of a search result. In this case, only when the function of a displayed protocol change button is set ON or an imaging protocol as a replacement destination is specified, an operation input can be accepted.

The present invention can provide a technique of allowing a radiation imaging system to easily change imaging protocols.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-001077, filed on Jan. 6, 2015, which is hereby incorporated by reference herein in its entirety.

What is claimed is:

1. A radiation imaging system including:
    a sensor unit configured to detect radiation transmitted through an object irradiated from a radiation generating apparatus controlled in accordance with imaging protocol including one or more parameters related to radiation imaging and obtains a radiation image corresponding to the radiation; and
    an information processing apparatus configured to perform control processing of the radiation generating apparatus in accordance with the imaging protocol and performs processing related to the radiation imaging for performing image processing of the radiation image obtained by the sensor unit, the information processing apparatus comprising:
    a holding unit configured to hold a plurality of imaging protocols; and
    a CPU configured to cause a display unit to display an image based on the radiation image obtained by the sensor unit in an image display area of the display unit, and to cause the display unit to display a protocol display area indicating the imaging protocol in an inspection information display portion located in an area different from the image display area of the display unit, wherein
    the CPU is configured to cause the display unit to display, in the protocol display area indicating a first imaging protocol displayed on the display unit, a GUI configured to perform replacement processing, according to an instruction from an operator, the first imaging protocol obtained as the imaging protocol from the plurality of imaging protocols held in the holding unit with a second imaging protocol specified as differing in some parameters from the first imaging protocol, and perform controlling for replacing the first imaging protocol with the second imaging protocol in accordance with an instruction from the operator to the GUI.

2. The system according to claim 1, wherein the CPU causes the display unit to display the user interface as a first user interface,
    the CPU causes the display unit to display, separately from the first user interface, a second user interface for selecting a candidate imaging protocol for replacing the first imaging protocol from a list of a plurality of imaging protocols held in the holding unit in accordance with an instruction from the operator, and
    the CPU replaces the first imaging protocol with an imaging protocol selected based on at least one of the first user interface and the second user interface.

3. The system according to claim 2, wherein the CPU causes the display unit to display an icon for replacing a parameter of the first imaging protocol for which radiation imaging is planned with another parameter of the second imaging protocol as the first user interface for each attribute in an instructable state, and
    the CPU replaces the first imaging protocol with the second imaging protocol with some parameters concerning an attribute of the icon being replaced with another parameter in accordance with selection of the icon by the operator.

4. The system according to claim 2, wherein the CPU causes the display unit to display a list of a plurality of imaging protocols held in the holding unit, in an instructable state, as the second user interface in place of a radiation image display area.

5. The system according to claim 1, wherein the CPU specifies, from the plurality of imaging protocols held in the holding unit, the second imaging protocol as an imaging protocol differing in at least one of an imaging direction, a body part of an object, laterality, an object size, a posture of the object, a clipping size, an irradiation condition for radiation and an image processing condition, as an attribute of a parameter relating to the first imaging protocol.

6. The system according to claim 1, wherein the CPU specifies the second imaging protocol differing in the some parameters of the first imaging protocol based on information, held as generation rule information of search condition for each attribute of the parameter, representing a relationship between a parameter as a replacement target and a parameter after replacement.

7. The system according to claim 1, wherein the CPU obtains the first imaging protocol and a protocol name of the first imaging protocol, and
    generates a search condition based on the protocol name and specifies the second imaging protocol with the some parameters being different parameters based on the search condition.

8. The system according to claim 1, wherein the CPU obtains the first imaging protocol as an identification code, and
specifies an identification code obtained by replacing a partial code value of the identification code with another code value as the second imaging protocol.

9. The system according to claim 1, wherein the CPU further specifies, from imaging protocols registered in advance as substitute candidates for each of the imaging protocols, an imaging protocol as a substitute candidate registered with respect to the first imaging protocol,
causes the display unit to further display an imaging protocol as the substitute candidate in an instructable state, and
the CPU replaces the first imaging protocol with an instructed imaging protocol when an imaging protocol as the substitute candidate is instructed by an operator.

10. An information processing apparatus that performs control processing for controlling a radiation generating apparatus configured to irradiate an object with radiation in accordance with imaging protocol including one or more parameters related to radiation imaging and performs processing related to the radiation imaging for performing image processing of a radiation image obtained by a sensor unit that detects radiation transmitted through an object irradiated from the radiation generating apparatus and obtains the radiation image corresponding to the radiation, the information processing apparatus comprising:
a holding unit configured to hold a plurality of imaging protocols; and
a CPU configured to cause a display unit to display an image based on the radiation image obtained by the sensor unit in an image display area of the display unit, and to cause the display unit to display a protocol display area indicating the imaging protocol in an inspection information display portion located in an area different from the image display area of the display unit, wherein
the CPU is configured to cause the display unit to display, in the protocol display area indicating a first imaging protocol displayed on the display unit, a GUI configured to perform replacement processing, according to an instruction from an operator, the first imaging protocol obtained as the imaging protocol from the plurality of imaging protocols held in the holding unit with a second imaging protocol specified as differing in some parameters from the first imaging protocol, and perform controlling for replacing the first imaging protocol with the second imaging protocol in accordance with an instruction from the operator to the GUI.

11. An information processing method performed by an information processing apparatus in an information processing system, wherein the information processing system including: a sensor unit that detects radiation transmitted through an object irradiated from a radiation generating apparatus controlled in accordance with imaging protocol including one or more parameters related to radiation imaging and obtains a radiation image corresponding to the radiation; and the information processing apparatus that performs control processing of the radiation generating apparatus in accordance with the imaging protocol and performs processing related to the radiation imaging for performing image processing of the radiation image obtained by the sensor unit, the information processing apparatus, the method comprising:

obtaining a first imaging protocol as the imaging protocol;
specifying, from a plurality of imaging protocols held in a holding unit, a second imaging protocol differing in some parameters from the first imaging protocol obtained in the obtaining;
displaying in an image display area an image based on the radiation image and causing a display unit to display a protocol display area indicating the imaging protocol in an inspection information display portion located in an area different from the image display area;
displaying, in the protocol display area indicating the first imaging protocol displayed on the display unit, a GUI configured to perform replacement processing, according to an instruction from an operator, the first imaging protocol with the second imaging protocol; and
replacing the first imaging protocol with the second imaging protocol in accordance with an instruction from the operator to the GUI.

12. An information processing method performed by an information processing apparatus that performs processing related to radiation imaging for performing image processing of a radiation image obtained by a sensor unit that obtains the radiation image corresponding to radiation by detecting radiation transmitted through an object irradiated from a radiation generating apparatus controlled in accordance with imaging protocol including one or more parameters related to radiation imaging and performs control processing for controlling the radiation generating apparatus in accordance with the imaging protocol, the method comprising:
obtaining a first imaging protocol as the imaging protocol;
specifying, from a plurality of imaging protocols held in a holding unit, a second imaging protocol differing in some parameters from the first imaging protocol obtained in the obtaining;
displaying in an image display area an image based on the radiation image and causing a display unit to display a protocol display area indicating the imaging protocol in an inspection information display portion located in an area different from the image display area;
displaying, in the protocol display area indicating the first imaging protocol displayed on the display unit, a GUI configured to perform replacement processing, according to an instruction from an operator, the first imaging protocol with the second imaging protocol; and
replacing the first imaging protocol with the second imaging protocol in accordance with an instruction from the operator to the GUI.

13. A non-transitory computer-readable storage medium storing a computer program for causing a computer to perform an information processing method according to claim 11.

14. A non-transitory computer-readable storage medium storing a computer program for causing a computer to perform an information processing method according to claim 12.

15. A radiation imaging system including:
a sensor unit configured to detect radiation transmitted through an object irradiated from a radiation generating apparatus controlled in accordance with imaging protocol including one or more parameters related to radiation imaging and obtains a radiation image corresponding to the radiation; and
an information processing apparatus configured to perform control processing of the radiation generating apparatus in accordance with the imaging protocol and performs processing related to the radiation imaging for performing image processing of the radiation image obtained by the sensor unit, the information processing apparatus comprising:

a holding unit configured to hold a plurality of imaging protocols; and a CPU configured to cause a display unit to display an image based on the radiation image obtained by the sensor unit in an image display area of the display unit, and to cause the display unit to display a protocol display area indicating the imaging protocol in an inspection information display portion located in an area different from the image display area of the display unit, wherein the CPU is configured to cause the display unit to display, in the protocol display area indicating a first imaging protocol displayed on the display unit, a GUI configured to perform replacement processing, according to an instruction from an operator, the first imaging protocol obtained as the imaging protocol from the plurality of imaging protocols held in the holding unit with a second imaging protocol specified as differing in some parameters from the first imaging protocol, and perform controlling for replacing the first imaging protocol with the second imaging protocol in accordance with an instruction from the operator to the GUI.

16. An information processing apparatus that performs control processing for controlling a radiation generating apparatus configured to irradiate an object with radiation in accordance with imaging protocol including one or more parameters related to radiation imaging and performs processing related to the radiation imaging for performing image processing of a radiation image obtained by a sensor unit configured to detect radiation transmitted through an object irradiated from the radiation generating apparatus and obtains the radiation image corresponding to the radiation, the information processing apparatus comprising:

a holding unit configured to hold a plurality of imaging protocols; and a CPU configured to cause a display unit to display an image based on the radiation image obtained by the sensor unit in an image display area of the display unit, and to cause the display unit to display a protocol display area indicating the imaging protocol in an inspection information display portion located in an area different from the image display area of the display unit, wherein the CPU is configured to cause the display unit to display, in the protocol display area indicating a first imaging protocol displayed on the display unit, a GUI configured to perform replacement processing, according to an instruction from an operator, the first imaging protocol obtained as the imaging protocol from the plurality of imaging protocols held in the holding unit with a second imaging protocol specified as differing in some parameters from the first imaging protocol, and perform controlling for replacing the first imaging protocol with the second imaging protocol in accordance with an instruction from the operator to the GUI.

17. An information processing method performed by an information processing apparatus in an information processing system, wherein the information processing system including: a sensor unit that detects radiation transmitted through an object irradiated from a radiation generating apparatus controlled in accordance with imaging protocol including one or more parameters related to radiation imaging and obtains a radiation image corresponding to the radiation; and the information processing apparatus that performs control processing of the radiation generating apparatus in accordance with the imaging protocol and performs processing related to the radiation imaging for performing image processing of the radiation image obtained by the sensor unit, the information processing apparatus, the method comprising:

displaying in an image display area an image based on the radiation image and causing a display unit to display a protocol display area indicating the imaging protocol in an inspection information display portion located in an area different from the image display area;

displaying, in the protocol display area indicating a first imaging protocol displayed on the display unit, a GUI configured to perform replacement processing, according to an instruction from an operator, the first imaging protocol obtained as the imaging protocol among a plurality of imaging protocols held in a holding unit with a second imaging protocol differing from the first imaging protocol; and replacing the first imaging protocol with the second imaging protocol in accordance with an instruction from the operator to the GUI.

18. An information processing method performed by an information processing apparatus that performs processing related to radiation imaging for performing image processing of a radiation image obtained by a sensor unit that obtains the radiation image corresponding to radiation by detecting radiation transmitted through an object irradiated from a radiation generating apparatus controlled in accordance with imaging protocol including one or more parameters related to radiation imaging and performs control processing for controlling the radiation generating apparatus in accordance with the imaging protocol, the method comprising:

displaying in an image display area an image based on the radiation image and causing a display unit to display a protocol display area indicating the imaging protocol in an inspection information display portion located in an area different from the image display area;

displaying, in the protocol display area indicating a first imaging protocol displayed on the display unit, a GUI configured to perform replacement processing, according to an instruction from an operator, the first imaging protocol obtained as the imaging protocol among a plurality of imaging protocols held in a holding unit with a second imaging protocol differing from the first imaging protocol; and replacing the first imaging protocol with the second imaging protocol in accordance with an instruction from the operator to the GUI.

19. A non-transitory computer-readable storage medium storing a computer program for causing a computer to perform an information processing method according to claim 17.

20. A non-transitory computer-readable storage medium storing a computer program for causing a computer to perform an information processing method according to claim 18.

* * * * *